United States Patent [19]

Millar

[11] Patent Number: 4,552,591

[45] Date of Patent: Nov. 12, 1985

[54] OIL FIELD BIOCIDE COMPOSITION

[75] Inventor: Scott W. Millar, Webster Groves, Mo.

[73] Assignee: Petrolite Corporation, St. Louis, Mo.

[21] Appl. No.: 610,452

[22] Filed: May 15, 1984

[51] Int. Cl.$^4$ ............................................. C09D 5/14
[52] U.S. Cl. ............................ 106/18.33; 106/18.34; 106/18.35; 252/8.5 A; 252/8.5 C; 514/365
[58] Field of Search ............ 252/8.5 A, 8.5 C, 8.5 P, 252/8.55 E, 8.5 B; 424/270; 106/18.34, 18.35, 18.33

[56] References Cited

U.S. PATENT DOCUMENTS

| | | | |
|---|---|---|---|
| 2,504,404 | 4/1950 | Flenner | 424/286 |
| 3,326,748 | 6/1967 | Popoff et al. | 424/286 |
| 3,699,231 | 10/1972 | Werlein et al. | 424/286 |
| 3,929,561 | 12/1975 | Shema et al. | 106/18.33 |
| 4,093,440 | 6/1978 | Denninger et al. | 424/286 |
| 4,107,300 | 8/1978 | Nakamura et al. | 424/286 |
| 4,122,192 | 10/1978 | Fellows | 424/333 |
| 4,129,448 | 12/1978 | Greenfield et al. | 106/18.32 |
| 4,150,026 | 4/1979 | Miller et al. | 424/270 |
| 4,165,318 | 8/1979 | Greenfield et al. | 424/270 |
| 4,243,403 | 1/1981 | Lewis et al. | 106/15.05 |
| 4,295,932 | 10/1981 | Pocius | 210/764 |
| 4,332,799 | 6/1982 | Quinlan | 252/8.55 E |

*Primary Examiner*—Lorenzo B. Hayes
*Attorney, Agent, or Firm*—Robert E. Wexler

[57] ABSTRACT

There is provided a biocide composition for oil field fluid polymers and oil field water polymers. The composition comprises a biocide adsorbed on the surface of a solid, particulate adsorbent. The composition lessens personal and environmental contamination by spilled or splashed liquid biocides.

5 Claims, No Drawings

OIL FIELD BIOCIDE COMPOSITION

BACKGROUND OF THE INVENTION

A. Field of the Invention

This invention relates to the field of oil well stimulation, drilling and recovery.

In particular, the invention relates to biocides for oil field water treatment and as preservatives for polymers used in oil field fluids and, especially, to preservatives in solid form which inhibit the growth of bacteria in oil field waters and on polymers used in oil field well stimulation and drilling fluids.

Polymers are used in the oil industry in methods of well stimulation, drilling and recovery. In the use of polymers, for example, in water flood, fracturing and drilling fluids, the polymers are subjected to an environment conducive to bacterial growth. The growth of the bacteria on polymers used in such fluids can materially alter the physical characteristics of the fluids. For example, bacterial action can deteriorate the polymer, leading to loss of viscosity and subsequent ineffectiveness of the fluids. Fluids which are especially susceptible to bacterial degradation are those which contain polysaccharide and synthetic polymers. The term "oil field fluids" as used herein is meant to include those fluids having oil field applications and whose viscosity has been increased with polymers, whether polysaccharide and/or synthetic. The term "oil field waters" as used herein includes waters used in secondary recovery, and water used to hydrate the polymers and water used in tertiary or EOR (enhanced oil recovery) methods.

Although biocides have been used in the past to treat oil field waters and oil field fluids used in oil field operations, they have been used, predominantly, in liquid form and, due to their very nature, must be handled with caution to avoid eye and skin contact from splashing. Also, the use of liquid biocides risks contamination of potable water sources from spilled biocides. Accordingly, there is a need for a safer form of biocides to avoid personal and environmental contamination.

B. Prior Art

U.S. Pat. No. 3,699,231 discloses the use of an aldehyde/carbamate mixture to inhibit bacterial action. U.S. Pat. No. 3,929,561 discloses a biocide mixture of 5-chloro-2-methyl-4-isothiazole-e-one, 2-methyl-4-isothiazolin-e-one and a sulfone.

U.S. Pat. Nos. 4,129,448 and 4,165,318 disclose mildew stabilization of acrylic emulsion polymr paints by using 3-isothiazolones as mildewcides and formaldehyde to stabilize the isothiazolones.

U.S. Pat. No. 4,295,932 discloses a microbial inhibiting mixture of 5-chloro-2-methyl-4-isothiazolin-3-one, 2-methyl-4-isothiazolin-3-one and chlorine or chlorine dioxide.

SUMMARY OF THE INVENTION

According to this invention, there is provided a biocidal composition which is comprised of a biocide and a granular solid adsorbent.

Further, the present invention provides methods for inhibiting microbial growth in oil field waters and for inhibiting microbial corrosion and starch and polymer degradation in oil field fluids comprising incorporating into said water and/or fluids an effective amount of antimicrobial composition of the invention.

SPECIFIC EMBODIMENTS OF THE INVENTION

According to the present invention, there is provided a biocidal composition comprising (1) at least one biocide and (2) a solid, particulate adsorbent therefor.

Any biocide is useful in the compositions of the invention if the viscosity of the biocide is such that it will adhere to a solid adsorbent. There is no specific requirement for biocide viscosity since each biocide is unique in its effectiveness and ability to adhere to a solid adsorbent.

Biocides which have been used in the past include aldehydes, e.g. formaldehyde, p-formaldehyde, glutaraldehyde, triazines, thiones, hydroxyalkylaminoalkanols, e.g. 2-hydroxymethyl-amino methanol, thiocarbamates, thiocyanates, isothiazolones and the like. The isothiazolin-3-ones are the preferred biocides found useful in the compositions of the present invention.

Suitable isothiazolin-3-ones useful in the composition of the invention include 2-methyl-4-isothiazolin-3-one, 2 ethyl-4-isothiazolin-3-one, 2-propyl-4-isothiazolin-3-one, 2-butyl-4-isothiazolin-3-one, 2-amyl-4-isothiazolin-3-one, 5-chloro-2-methyl-4-isothiazolin-3-one, 5-bromo-2-methyl-4-isothiazolin-3-one, 5-iodo-2-methyl-4-isothiazolin-3-one, 5-chloro-2-butyl-4-isothiazolin-3-one, 5-bromo-2-ethyl-4-isothiazolin-3-one, 5-iodo-2-amyl-4-isothiazolin-3-one and similar analogs and homologs within the genus.

Preferably, the present invention utilizes a mixture of isothiazolin-3-ones comprising isothiazolin-3-ones wherein the 2 position is substituted by an alkyl group having from about 1 to about 5 carbon atoms, especially from about 1 to about 3 carbon atoms, preferably 1 carbon atom and wherein the five position may be substituted by a halogen group, for example iodo, chloro and bromo, especially chloro.

The weight ratio of halogenated isothiazolin-3-one to non-halogenated isothiazolin-3-one is from about 94% to about 64%, preferably from about 73% to about 88%, especially about 79%.

The adsorbents used in the compositions of the invention may be any of the well-known adsorbents having a high degree of surface area which are generally particulate, i.e. granular or bead-like in nature, and of sufficient integrity to avoid formation of a paste-like mass when contacted with the liquid biocide. Thus, common adsorbents which are useful include diatomaceous earth, silica, metal oxides such as alumina, bauxite, magnesia, iron oxides and the like, clays such as attapulgite, bone char, carbon, fuller's earth, zeolites, resins and waxes. Diatomaceous earth is preferred. The adsorbents should have a particle size of from about 9 micrometers to about 1200 micrometers. A useful average particle size is from about 150–700 micrometers.

The biocide-adsorbent compositions of the invention may be prepared in a variety of ways. For example, the biocide may be merely mixed with the adsorbent and used as such. Additionally, the adsorbent may be saturated with the biocide and subjected to filtration followed by comminution of the filter cake. Preferably, the adsorbent is added to a liquid/solid type blender which is vented and sealed. The blender is then activated and the biocide is gravity fed into the mixing chamber where a drip bar dispenses it over the adsorbent. The blender is allowed to run for 3–5 minutes or until all of the biocide has been thoroughly intermixed with the adsorbent. The blender is then shut down and the biocide-adsorbent composition is dispensed into an appropriate container.

The amount of biocide added to the adsorbent will depend on the particular biocide being used and its effectiveness at various activity levels. Thus, the concentrated biocide is customarily diluted to afford an activity level commensurate with bacterial inhibition. Further, a solution of 10% by weight biocide in appropriate solvent (10% active) has biocidal properties which will vary depending on the particular biocide and the amount of the solution which is added to a particular bacterial substrate. Accordingly, a biocide may be added to the adsorbent undiluted (100% active) or it may be diluted with solvent to a very low active concentration, e.g. 0.01% active. With regard to the preferred isothiazolin-3-ones, the pure biocide is usually diluted with water or water/alcohol to achieve levels of from about 0.015% to about 25% active, preferably from about 1.5% to about 15% active.

The amount of biocidal composition incorporated in a particular oil field water or oil field fluid polymer will vary widely as discussed above, depending upon the polymer itself, the particular inhibitor composition, the conditions of use of the water or polymer and the extent of prior contamination by bacteria, the time period of growth inhibition desired, general environment and the like. Thus, it is not possible to quantitatively delineate a minimum effective amount of the inhibiting composition. There is no maximum amount, although large excesses may not be desired from an economic standpoint.

The resulting biocidal composition is incorporated into polymers used in oil field fluids including, for example, starches, carboxymethycellulose polymers, guar gums, polysaccharides, and polyacrylamides, in an effective bacterial inhibiting amount. Thus, the composition is incorporated in an amount of from about 10 ppm (parts per million) of active biocide to about 1000 ppm, preferably from about 500 ppm, based on the total parts of solution to be treated. Thus, 10 ppm of a 10% active biocide affords 1 ppm of active ingredient and 10 ppm of 100% active biocide affords 10 ppm of active ingredient.

The biocidal preservative composition may be incorporated into the oil field water or oil field fluid polymer by adding the composition into the (1) water used for making the polymer solution, (2) concentrated polymer solution and/or (3) dilute polymer solution on a slug dose basis.

The preservative compositions of the invention are effective against aerobic bacteria and anaerobic bacteria. The isothiazolin-3-ones are especially effective against sulfate reducing bacteria, for example "Desulfovibrio" species, e.g. "*Desulfovibrio desulfurican*" and "Desulfotomaculum" species, e.g. "*Desulfotomaculum nigrificans*".

Examples of aerobic bacteria and anaerobic bacteria which are commonly found in oil field fluids and oil field waters and which are inhibited by the compositions of the present invention include "Pseudomonad" species, e.g. "*Pseudomonas fluorescens*", "Bacillus" species, e.g. "*Bacillus subtilis*", "Enterobacter" species, e.g. "*Enterobacter aerogenes*", "Serratia" species, e.g. "*Serratia marcesens*" and "Clostridia" species. Algae and fungi found in oil field waters and oil field fluids are also inhibited by the compositions of the invention.

The following examples illustrate specific embodiments of the present invention, including the best mode of practicing the invention. The examples are illustrative only and are not included by way of limitation.

EXAMPLE 1

A bactericide performance test was set up in an oil field fluid containing a synthetic polyacrylamide polymer. The fluid was taken from a micellar polymer flood in which the polymer was used to increase viscosity. The fluid was made up of approximately 500 ppm of a high molecular weight partially hydrolyzed polyacrylamide polymer in filtered fresh water. The fluid was contaminated with approximately 12,000 aerobic bacteria per milliliter.

An inhibitor composition was prepared consisting of a 50/50 mixture of 5-chloro-2-methyl-4-isothiazolin-3-one and 2-methyl-4-isothiazolin-3-one (1.5% active). The composition was added to the contaminated fluid. Samples were taken after 24 and 48 hour exposures and surviving aerobic bacteria were enumerated. The following results were obtained:

TABLE 1

| Compound | Concentration (ppm) | Surviving bacteria/ml 24 Hours | 48 Hours |
|---|---|---|---|
| 1.5% isothiazolin-3-one mixture | 50 | 11,000 | 45,000 |
|  | 75 | 2,500 | 53,000 |
|  | 100 | 8,100 | 52,000 |
|  | 200 | 1,500 | 1,800 |
| Control (no inhibitor) | 0 | 120,000 | 89,000 |

These results show the effectiveness of the inhibitor composition in liquid form. The inhibitor mixture controlled bacterial growth at a concentration of between about 50 and about 200 ppm inhibitor.

EXAMPLE 2

A bactericide performance test was set up in an oil field fluid containing an emulsion polyacrylamide polymer. The fluid was taken from a micellar polymer flood and was composed of approximately 3000 ppm of a 30% active partially hydrolyzed polyacrylamide emulsion polymer in fresh water. The fluid contained approximately 100,000 aerobic bacteria per milliliter and 1000 anaerobic sulfate reducing bacteria per milliliter.

The bactericidal activity of an inhibitor mixture of the invention was compared to a control (no inhibitor). Samples were taken after three and seven days exposure and surviving aerobic and sulfate reducing bacteria enumerated. The following table presents the results of the test:

TABLE 2

| | | Surviving Bacteria/ml | | | |
| | | 3 Days | | 7 Days | |
| Compound | Concentration (ppm) | Aerobes | Reducers | Aerobes | Reducers |
|---|---|---|---|---|---|
| 1.5% Isothiazolin-3-ones mixture | 50 | 10,000 | 1-9 | 100,000 | 100 |
|  | 75 | 5,000 | 1-9 | 15,000 | 100 |
|  | 100 | 1,000 | 1-9 | 1,000 | 1-9 |
|  | 150 | 30 | 90-99 | 0 | 0 |

TABLE 2-continued

| | | Surviving Bacteria/ml | | | |
|---|---|---|---|---|---|
| | | 3 Days | | 7 Days | |
| Compound | Concentration (ppm) | Aerobes | Reducers | Aerobes | Reducers |
| Control | 0 | 14,000,000 | 1000 | 29,000,000 | 1000 |

The results show the antibacterial composition containing isothiazolin-3-ones mixture to be effective.

The antimicrobial mixture effectively protected the polymer solution at a rate of between about 50 to about 150 ppm product.

EXAMPLE 3

This example illustrates the comparative effectiveness of various concentrations of (a) a 50/50 liquid mixture of 5-chloro-2-methyl-4-isothiazolin-3-one and 2-methyl-4-isothiazolin-3-one (7% active) and (b) the same mixture of isothiazolin-3-ones adsorbed on Celite 545 (Johns-Manville) diatomaceous earth against typical fracturing fluid bacteria in a hydroxypropyl guar fracturing fluid (Jaguar HP-8, Stein-Hall Specialty Chemicals). The kill rate date are set forth in Table 3, below:

TABLE 3

| Compound | Concentration (ppm) | Kill Rate (%) 24 Hrs. | Kill Rate (%) 72 Hrs. |
|---|---|---|---|
| Isothiazolin-3-ones (7% active) | 10 | 85 | 100 |
| | 25 | 85 | 100 |
| | 150 | 95 | 100 |
| | 200 | 99 | 100 |
| Composition of Invention (7% active) | 10 | 85 | 100 |
| | 25 | 90 | 100 |
| | 150 | 95 | 100 |
| | 200 | 99 | 100 |
| Control | 0 | 0 | 0 |

The data illustrate that there is no difference in effectiveness when the liquid biocide is adsorbed on the diatomaceous earth.

EXAMPLE 4

This example illustrates the effectiveness of a composition of the invention, comprising a 7% active mixture of a 50/50 mixture of the isothiazolin-3-ones of Example 3 adsorbed on diatomaceous earth (Celite 545), at various concentrations as against typical field bacteria in hydroxypropyl guar fracturing fluids. The starting plate count was 540 colonies/ml. The data are set forth in Table 4, below:

TABLE 4

| Compound | Concentration (ppm) | Kill Rate (%) 24 Hrs. | Kill Rate (%) 48 Hrs. |
|---|---|---|---|
| Composition of Invention | 25 | 99.8 | 96.0 |
| | 50 | 99.9 | 99.9 |
| | 100 | 99.9 | 99.9 |
| | 200 | 99.9 | 99.9 |
| | 250 | 99.9 | 99.9 |
| Control | 0 | 0 | 0 |

The data illustrate that a 7% active concentration of the biocide on diatomaceous earth is effective at a concentration of 25 ppm or greater against field bacteria in a hydroxypropyl guar fracturing fluid.

EXAMPLE 5

This example illustrates the effectiveness of the compositions of the invention against bacteria in drilling mud.

A sample of drilling mud (Davis Mud and Chemical Co.) was treated with a 7% active concentration of a 50/50 mixture of the isothiazolin-3-ones of Example 3 on Celite 545. The initial bacterial plate count of the mud was 18,000/ml. The data are set forth as Table 5, below:

TABLE 5

| Compound | Concentration (ppm) | % Kill Plate Density Method |
|---|---|---|
| Composition of Invention | 50 | 70 |
| | 100 | 85 |
| | 150 | 95 |
| | 250 | 98 |
| Control | 0 | 0 |

The data illustrate that the composition of the invention is effective against bacteria in a drilling mud.

EXAMPLE 6

This example illustrates the effectiveness of the composition of the invention against typical field bacteria in a salt water based drilling mud.

A sample of salt water based drilling mud (Drilling Mud, Inc.) was innoculated with typical wild field mud bacteria and incubated until the population reached $5.1 \times 10^4$ bacteria/ml. Fifty (50) ml. aliquots were then treated with varying concentrations of a composition of the invention as described in Example 3 and the results were compared with varying concentrations of liquid isothiazolin-3-one mixture and other liquid commercial biocides. The results are set forth in Table 6, below:

TABLE 6

| Compound | Concentrations (ppm) | % Kill (Days) 1 | 2 | 3 | 4 |
|---|---|---|---|---|---|
| Composition of Invention (Ex. 3) | 25 | 20 | 20 | 80 | 20 |
| | 50 | 30 | 30 | 90 | 50 |
| | 100 | 40 | 40 | 90 | 70 |
| | 150 | 50 | 70 | 90 | 70 |
| Liquid isothiazolinones of Ex. 3 1.5% active) | 100 | 20 | 40 | 80 | 20 |
| | 250 | 30 | 50 | 90 | 40 |
| | 500 | 40 | 60 | 90 | 50 |
| | 1000 | 50 | 75 | 90 | 70 |
| Glutaraldehyde (50% active) | 50 | 80 | 95 | 99.9 | 99.9 |
| | 100 | 99 | 99.9 | 99.9 | 99.9 |
| | 250 | 99.9 | 99.9 | 99.9 | 99.9 |
| | 500 | 99.9 | 99.9 | 99.9 | 99.9 |
| p-Formaldehyde (100% active) | 250 | 99 | 99.9 | 99.9 | 99.9 |
| | 500 | 99.9 | 99.9 | 99.9 | 99.9 |
| | 750 | 99.9 | 99.9 | 99.9 | 99.9 |
| | 1000 | 99.9 | 99.9 | 99.9 | 99.9 |
| Formaldehyde (33% active) | 100 | 50 | 90 | 99.9 | 99 |
| | 250 | 75 | 98 | 99.9 | 99.9 |
| | 500 | 90 | 99 | 99.9 | 99.9 |
| | 1000 | 99.9 | 99.9 | 99.9 | 99.9 |
| Methylene bis-thiocyanate (10% active) | 50 | 20 | 70 | 75 | 80 |
| | 100 | 20 | 75 | 85 | 95 |
| | 250 | 30 | 80 | 90 | 95 |
| | 500 | 45 | 90 | 90 | 95 |
| Diothiocarbamate | 250 | 50 | 80 | 90 | 80 |

TABLE 6-continued

| Compound | Concentrations (ppm) | % Kill (Days) | | | |
|---|---|---|---|---|---|
| | | 1 | 2 | 3 | 4 |
| (15% active) | 500 | 75 | 85 | 95 | 85 |
| | 750 | 80 | 95 | 99.9 | 90 |
| | 1000 | 90 | 98 | 99.9 | 95 |

The results indicate that the compositions of the invention is as effective as the liquid isothiazolin-3-one and that other commercial liquid biocides are also effective and would be expected, on the basis of examples 1, 2 and 3, to be effective if used in conjunction with an adsorbent. The biocide composition of the invention presents no liquid handling problems and, thus, no personal or environmental problems associated with, for example, spilled or splashed liquid biocides.

The compositions of the invention find utility in the treatment of oil field water and oil field fluid polymers, e.g. polyacrylamides and polysaccharides, in the preservation of guar gum, hydroxypropyl guar gum and carboxymethylcellulose polymers used in fracturing fluids for oil well stimulation, and in the preservation of starches, guar gum, hydroxypropyl guar gum and carboxymethylcellulose polymers used in such fluids.

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth herein but rather that the claims be construed as encompassing all the features of patentable novelty which reside in the present invention, including all features which which would be treated as equivalents thereof by those skilled in the art to which the invention pertains.

I claim:

1. A method of inhibiting bacterial growth in oil field fluids comprising adding thereto an effective bacterial inhibiting amount of a biocide consisting essentially of a mixture of 5-chloro-2-methyl-4-isothiazolin-3-one and 2-methyl-4-isothiazolin-3-one, the weight ratio of the former to the latter being from about 94 percent to about 64 percent, adsorbed on a solid, particulate adsorbent.

2. Method of claim 1 wherein said fluid is a fracturing fluid.

3. Method of claim 1 wherein said fluid is a drilling fluid.

4. Method of claim 1 wherein said fluid is a water flood system.

5. Method of claim 1 wherein said fluid is an oil field water.

* * * * *